(12) United States Patent
Ramalingam et al.

(10) Patent No.: US 10,752,603 B2
(45) Date of Patent: Aug. 25, 2020

(54) PURIFICATION OF OXYDIPHTHALIC ANHYDRIDES

(71) Applicant: SABIC Global Technologies, B.V., Bergen op Zoom (NL)

(72) Inventors: Hariharan Ramalingam, Bangalore (IN); Tarun Kumar Pal, Bangalore (IN); Meerakani Mohamed Ali Sait, Bangalore (IN); Thomas Link Guggenheim, Mt. Vernon, IN (US); Lioba Maria Kloppenburg, Mt. Vernon, IN (US)

(73) Assignee: SABIC GLOBAL TECHNOLOGIES, B.V., Bergen op Zoom (NL)

( * ) Notice: Subject to any disclaimer, the term of this patent is extended or adjusted under 35 U.S.C. 154(b) by 19 days.

(21) Appl. No.: 16/271,207

(22) Filed: Feb. 8, 2019

(65) Prior Publication Data
US 2019/0256485 A1    Aug. 22, 2019

(30) Foreign Application Priority Data

Feb. 19, 2018    (EP) .................................... 18157359

(51) Int. Cl.
| | | |
|---|---|---|
| *C07D 307/89* | (2006.01) | |
| *C07D 307/80* | (2006.01) | |
| *C08G 73/10* | (2006.01) | |
| *C07D 407/12* | (2006.01) | |

(52) U.S. Cl.
CPC .......... *C07D 307/80* (2013.01); *C07D 407/12* (2013.01); *C08G 73/10* (2013.01); *C08G 73/1053* (2013.01); *C08G 73/1082* (2013.01); *C08G 73/1021* (2013.01); *C08G 73/1046* (2013.01)

(58) Field of Classification Search
CPC ...... C07C 39/42; C07D 277/34; C07D 307/80
See application file for complete search history.

(56) References Cited

U.S. PATENT DOCUMENTS

| | | | |
|---|---|---|---|
| 4,874,835 A | 10/1989 | Berdahl | |
| 9,127,127 B2 | 9/2015 | Guggenheim et al. | |
| 2006/0293528 A1 | 12/2006 | Stella et al. | |
| 2007/0073063 A1* | 3/2007 | Stella ................... | C07D 209/48 548/461 |
| 2007/0117990 A1* | 5/2007 | Pressman ............. | C07D 307/89 549/241 |
| 2009/0247725 A1* | 10/2009 | Bernabe ............. | C08G 73/1046 528/271 |
| 2014/0094535 A1 | 4/2014 | Guggenheim et al. | |

FOREIGN PATENT DOCUMENTS

| | | |
|---|---|---|
| EP | 1674443 B1 | 6/2006 |
| WO | 2009120212 A1 | 10/2009 |
| WO | 2014055747 A1 | 4/2014 |
| WO | 2017117343 A1 | 7/2017 |

* cited by examiner

*Primary Examiner* — Gregory Listvoyb
(74) *Attorney, Agent, or Firm* — Cantor Colburn LLP

(57) ABSTRACT

A process for the purification of an oxydiphthalic anhydride includes contacting a mixture of an oxydiphthalic anhydride and at least one of the corresponding oxydiphthalic diacid, a corresponding oxydiphthalic tetraacid, a halophthalic anhydride, and a catalyst with a solvent to provide a slurry. The solvent is capable of solubilizing the corresponding oxydiphthalic diacid, the corresponding oxydiphthalic tetraacid, the halophthalic anhydride, and the catalyst at a temperature of 15 to 50° C., and the oxydiphthalic anhydride is substantially insoluble in the solvent at this temperature. The oxydiphthalic anhydride can be isolated from the slurry. A purified oxydiphthalic anhydride and a polyetherimide prepared therefrom are also disclosed.

12 Claims, No Drawings

PURIFICATION OF OXYDIPHTHALIC ANHYDRIDES

BACKGROUND

Oxydiphthalic anhydride is commonly used as a monomer component to form a unique class of high temperature polyetherimides. Oxydiphthalic anhydrides can generally be prepared by coupling two halophthalic anhydrides in the presence of an inorganic carbonate, a solvent, and a catalyst. The crude product of such a reaction often includes the solvent, unreacted starting materials, catalyst, and other impurities, which must be separated from the oxydiphthalic anhydride prior to its use in polymer synthesis. Residual impurities have been shown to have an adverse effect on the thermal stability of the resulting polymers.

The purification of anhydrides has thus been the focus of extensive research and development. Despite the previous research efforts, there remains a need for an improved purification process for oxydiphthalic anhydrides. It would be particularly advantageous to provide a more efficient method for the purification of oxydiphthalic anhydrides that could remove substantially all residual reactants, reaction intermediates, and residual catalyst.

BRIEF DESCRIPTION

A process for purification of an oxydiphthalic anhydride comprises contacting a mixture comprising an oxydiphthalic anhydride, and at least one of a corresponding oxydiphthalic diacid, a corresponding oxydiphthalic tetraacid, a halophthalic anhydride, and a catalyst, with a solvent to provide a slurry; wherein the solvent is capable of solubilizing at least one of the corresponding oxydiphthalic diacid, the corresponding oxydiphthalic tetraacid, the halophthalic anhydride, and the catalyst at a temperature of 15 to 50° C.; and wherein the oxydiphthalic anhydride is substantially insoluble in the solvent at a temperature of 15 to 50° C.; and isolating the oxydiphthalic anhydride from the slurry.

An oxydiphthalic anhydride prepared according to the process is also described.

An oxydiphthalic anhydride comprises less than or equal to 5 wt % of a corresponding oxydiphthalic tetraacid; less than or equal to 2 wt % of a corresponding oxydiphthalic diacid; less than or equal to 1 wt % of a halophthalic anhydride; and less than or equal to 0.09 wt %, or less than 0.05 wt %, or less than 0.01 wt % of a catalyst; wherein weight percent is based on the total weight of the oxydiphthalic anhydride; and wherein the oxydiphthalic anhydride has an APHA color value of less than 137.

A polyetherimide prepared by polymerizing the oxydiphthalic anhydride is also described.

The above described and other features are exemplified by the following detailed description.

DETAILED DESCRIPTION

Disclosed herein is an improved process for the purification of an oxydiphthalic anhydride. The process employs one or more washes of the oxydiphthalic anhydride with a solvent that can selectively solubilize an impurity present in the oxydiphthalic anhydride (e.g., a residual reactant, reaction intermediate, or catalyst). The oxydiphthalic anhydride is substantially insoluble in the solvent, so the oxydiphthalic anhydride can be effectively washed with minimal loss of yield. Advantageously, the purification of the oxydiphthalic anhydride can be conducted at temperature less than 50° C., for example at room temperature. The efficient purification process described herein represents a substantial improvement in the purification of oxydiphthalic anhydrides.

Accordingly, a process for purification of an oxydiphthalic anhydride comprises contacting a mixture comprising an oxydiphthalic anhydride and at least one of a corresponding oxydiphthalic diacid, a corresponding oxydiphthalic tetraacid, a halophthalic anhydride, and a catalyst with a solvent to provide a slurry.

The oxydiphthalic anhydride can be of the formula (1)

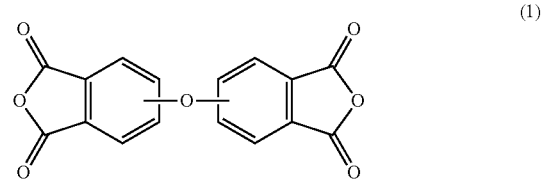

wherein the divalent bonds of the —O— group can be in the 3,3',3,4',4,3' or 4,4' positions. For example, the oxydiphthalic anhydride can be 4,4'-oxydiphthalic anhydride, 3,4'-oxydiphthalic anhydride, 3,4'-oxydiphthalic anhydride, 3,3'-oxydiphthalic anhydride or a combination comprising at least one of the foregoing, and preferably is 4,4'-oxydiphthalic anhydride.

The corresponding oxydiphthalic tetraacid is of the formula (2)

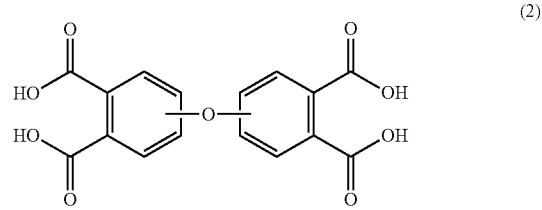

wherein the divalent bonds of the —O— group can be in the 3,3',3,4',4,3' or 4,4' positions. For example, the oxydiphthalic tetraacid can comprise 4,4'-oxydiphthalic tetraacid, 3,4'-oxydiphthalic tetraacid, 3,4'-oxydiphthalic tetraacid, 3,3'-oxydiphthalic tetraacid or a combination comprising at least one of the foregoing, preferably 4,4'-oxydiphthalic tetraacid.

The corresponding oxydiphthalic diacid is of the formula (3)

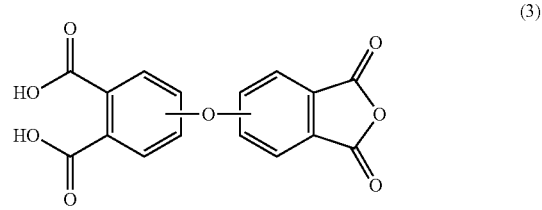

wherein the divalent bonds of the —O— group can be in the 3,3',3,4',4,3' or 4,4' positions. For example, the corresponding oxydiphthalic diacid can comprise 4,4'-oxydiphthalic diacid, 3,4'-oxydiphthalic diacid, 3,4'-oxydiphthalic diacid, 3,3'-oxydiphthalic diacid or a combination comprising at least one of the foregoing, preferably 4,4'-oxydiphthalic diacid.

The halophthalic anhydride can be of the formula (4)

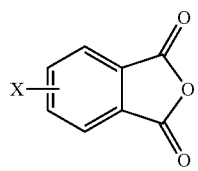

wherein X is fluoro, chloro, bromo, iodo, or a combination comprising at least one of the foregoing. Specific examples of suitable halophthalic anhydrides include 3-fluorophthalic anhydride, 4-fluorophthalic anhydride, 3-chlorophthalic anhydride, 4-chlorophthalic anhydride, 3-bromophthalic anhydride, 4-bromophthalic anhydride, 3-iodophthalic anhydride, and 4-iodophthalic anhydride. In some embodiments, X is chloro, and the halophthalic anhydride is a chlorophthalic anhydride. Exemplary chlorophthalic anhydrides can include 3-chlorophthalic anhydride, 4-chlorophthalic anhydride, or a combination comprising at least one of the foregoing, preferably 4-chlorophthalic anhydride.

The catalyst can be a phase transfer catalyst, for example, as described in U.S. Pat. No. 9,127,127. For example, the catalyst can include guanidinium salts, pyridinium salts, imidazolium salts, tetra($C_{7-24}$ arylalkylene)ammonium salts, dialkyl heterocycloaliphatic ammonium salts, bis-alkyl quaternary ammonium salts, ($C_{7-24}$arylalkylene)($C_{1-16}$alkyl) phosphonium salts, ($C_{6-24}$aryl) or ($C_{1-16}$alkyl) phosphonium salts, phosphazenium salts, and combinations comprising at least one of the foregoing. In some embodiments, the catalyst can be a hexa($C_{1-16}$alkyl)guanidinium halide, a ($C_{6-24}$aryl) or ($C_{1-16}$alkyl) phosphonium salt, a pyridinium salt, a tetra($C_{7-24}$ arylalkylene)ammonium salt, or a combination comprising at least one of the foregoing. In some embodiments, the catalyst preferably comprises a hexa($C_{1-16}$alkyl)guanidinium halide or a tetra($C_{6-24}$aryl) phosphonium halide. For example, the catalyst can be tetraethylammonium bromide, tetraethylammonium acetate, tetrabutylammonium bromide, tetrapropylammonium bromide, tetrabutylammonium chloride, tetrabutylammonium fluoride, tetrabutylammonium acetate, tetrahexylammonium chloride, tetraheptylammonium chloride, Aliquat 336 phase transfer catalyst (methyltrioctylammonium chloride, manufactured by the General Mills Company), tetrabutylphosphonium bromide, tetraphenylphosphonium bromide, tetrabutylphosphonium chloride, hexaethylguanidinium chloride, and the like. A pyridinium salt, for example a bis-aminopyridinium salt can also be used.

The mixture can include less than or equal to 5 weight percent (wt %), or less than or equal to 1 wt % of the at least one of the corresponding oxydiphthalic diacid, the corresponding oxydiphthalic tetraacid, the halophthalic anhydride, and the catalyst, wherein weight percent is based on the total weight of the mixture.

In a specific embodiment, the mixture is a product mixture obtained by a process that includes combining a halophthalic anhydride and an organic solvent with a catalyst to provide a first solution; adding an alkali metal carbonate to the first solution under conditions effective to provide a second solution comprising a crude oxydiphthalic anhydride product; isolating the crude oxydiphthalic anhydride product from the second solution, preferably by cooling the second solution to a temperature effective to precipitate the oxydiphthalic anhydride and filtering the second solution to provide the crude oxydiphthalic anhydride product; combining the crude oxydiphthalic anhydride product with water and an organic acid under conditions effective to hydrolyze the oxydiphthalic anhydride to the corresponding oxydiphthalic tetraacid; isolating the oxydiphthalic tetraacid; and condensing the oxydiphthalic tetraacid to provide the oxydiphthalic anhydride product mixture. Conditions for converting the oxydiphthalic tetraacid to the corresponding oxydiphthalic anhydride can be dependent upon the identity of the anhydride and can be readily determined by one of ordinary skill in the art. For example, useful temperatures can be 160 to 300° C., or 180 to 240° C. or 200 to 220° C. The conversion of the tetraacid to dianhydride is a cyclization with the concurrent formation of water. For example, the tetraacid can be condensed by refluxing in the presence of a dehydrating agent, for example acetic anhydride. In some embodiments, a temperature of 100 to 225° C. and a pressure of 0 to 1 MPa can be used.

In another specific embodiment, the mixture is a product mixture obtained by a process comprising combining a halophthalic anhydride and an organic solvent with a catalyst to provide a first solution adding an alkali metal carbonate to the first solution under conditions effective to provide a second solution comprising the oxydiphthalic anhydride; and filtering the second solution at a temperature of 180 to 190° C. to provide the oxydiphthalic product mixture.

The solvent used to provide the slurry is capable of solubilizing the corresponding oxydiphthalic diacid, the corresponding oxydiphthalic tetraacid, the halophthalic anhydride, and the catalyst at a temperature of 15 to 50° C., preferably at room temperature. Furthermore, the oxydiphthalic anhydride is substantially insoluble in the solvent at a temperature of 15 to 50° C., preferably at room temperature. Accordingly, the slurry that is provided comprises precipitated oxydiphthalic anhydride and solubilized impurity (e.g., corresponding oxydiphthalic diacid, corresponding oxydiphthalic tetraacid, halophthalic anhydride, 4-halodiacid, 4-hydroxyphalic anhydride, or catalyst). In some embodiments, the solvent is preferably methanol.

The solvent can be added in an amount such that the oxydiphthalic anhydride is present in the slurry in an amount of 10 to 30 wt %, based on the total weight of the slurry.

The method further comprises isolating the oxydiphthalic anhydride from the slurry. As described above, the oxydiphthalic anhydride is substantially insoluble in the solvent, and is therefore present in the slurry as a precipitate. In some embodiments, isolating the oxydiphthalic anhydride comprises filtering the slurry.

The contacting and the isolating can optionally be repeated one or more times, for example until a desired purity of the oxydiphthalic anhydride is obtained. For example, the contacting and the isolating can be repeated until the oxydiphthalic anhydride isolated from the slurry has a purity of greater than 97%, or greater than 99%, or greater than 99.4%.

In a specific embodiment, the mixture comprises 4,4'-oxydiphthalic anhydride and at least one of 4,4'-oxydiphthalic tetraacid, 4,4'-oxydiphthalic diacid, 4-chlorophthalic anhydride, and hexaethylguanidinium chloride, the solvent is methanol, and isolating the oxydiphthalic anhydride comprises filtering the slurry. The process further comprises repeating the contacting and the isolating one to three times to provide an isolated oxydiphthalic anhydride comprising, based on the total weight of the isolated oxydiphthalic anhydride.

An oxydiphthalic anhydride represents another aspect of the present disclosure. The oxydiphthalic anhydride can be purified according to the method described above. An oxydiphthalic anhydride independent of the purification method is also disclosed. Advantageously, the oxydiphthalic anhydride comprises less than or equal to 5 wt % of a corresponding oxydiphthalic tetraacid; less than or equal to 2 wt % of a corresponding oxydiphthalic diacid; less than or equal to 1 wt % of a halophthalic anhydride; and less than or equal to 0.09 wt %, or less than 0.05 wt %, or less than 0.01 wt % of a catalyst, wherein weight percent is based on the total weight of the oxydiphthalic anhydride.

The oxydiphthalic anhydride can have an APHA color value of less than 140 or less than 137 or less than 135, as determined according to ASTM D1209. For example, a 10% solution of the oxydiphthalic anhydride in a suitable solvent (e.g., dimethylformamide) can be used to measure APHA color using a Macbeth colorimeter. In some embodiments, the isolated oxydiphthalic anhydride is color stable. As used herein "color stable" means that the measured APHA color value is not significantly different before and after subjecting the isolated oxydiphthalic anhydride to a heat treatment. The color stability of the isolated oxydiphthalic anhydride and a method for the determination thereof are further described in the working examples below.

The oxydiphthalic anhydrides can be particularly useful for the manufacture of a polyetherimide. Specifically, polymerization of the oxydiphthalic anhydride with an organic diamine of the formula (5)

$$H_2N-R-NH_2 \quad (5)$$

provides the polyetherimide. In formula (5), each R can be the same or different, and is a substituted or unsubstituted divalent organic group, such as a $C_{6-20}$ aromatic hydrocarbon group, a straight or branched chain $C_{2-20}$ alkylene group, a $C_{3-8}$ cycloalkylene group, in particular a halogenated derivative of any of the foregoing. In some embodiments R is divalent group of one or more of the following formulas (6)

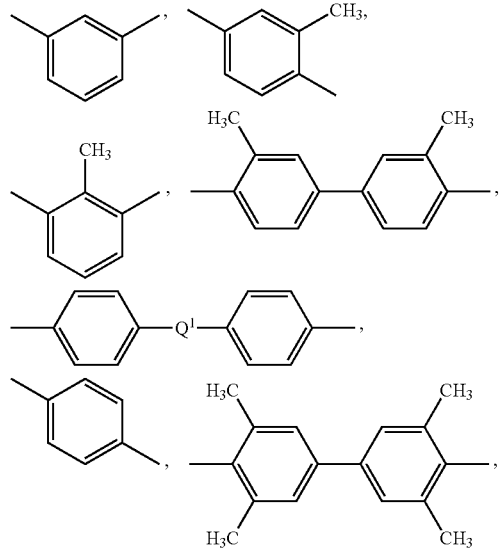

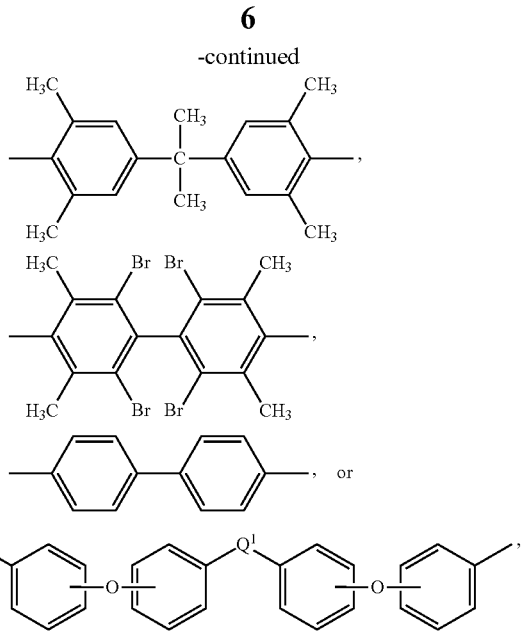

wherein $Q^1$ is —O—, —S—, —C(O)—, —SO$_2$—, —SO—, —P(R$^a$)(=O)— wherein R$^a$ is a $C_{1-8}$ alkyl or $C_{6-12}$ aryl, —C$_y$H$_{2y}$— wherein y is an integer from 1 to 5 or a halogenated derivative thereof (which includes perfluoroalkylene groups), or —(C$_6$H$_{10}$)$_z$— wherein z is an integer from 1 to 4. In some embodiments R is m-phenylene, p-phenylene, or a diarylene sulfone, in particular bis(4,4'-phenylene)sulfone, bis(3,4'-phenylene)sulfone, bis(3,3'-phenylene)sulfone, or a combination comprising at least one of the foregoing. In some embodiments, at least 10 mole percent (mol %) of the R groups contain sulfone groups, and in other embodiments no R groups contain sulfone groups.

The polyetherimide comprises 2 to 1000, or 5 to 500, or 10 to 100 repeating units of formula (7)

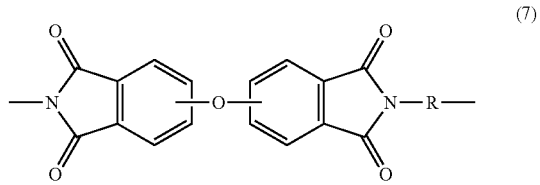

wherein each R is the same or different, and is as described in formula (5) above. Further in formula (7), the divalent bonds of the —O— group are in the 3,3',3,4',4,3', or the 4,4' positions. In an embodiment in formula (7), R is m-phenylene or p-phenylene. Alternatively, the polyetherimide can be a copolymer comprising additional structural polyetherimide units of formula (7) wherein at least 50 mol % of the R groups are bis(3,4'-phenylene)sulfone, bis(3,3'-phenylene)sulfone, bis(4,4'-phenylene)sulfone, or a combination comprising at least one of the foregoing, and the remaining R groups are p-phenylene, m-phenylene or a combination comprising at least one of the foregoing.

In some embodiments, the polyetherimide is a copolymer that optionally comprises additional structural imide units that are not polyetherimide units, for example imide units of formula (8)

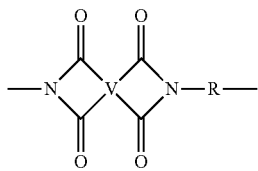

(8)

wherein R is as described in formula (5) and each V is the same or different, and is a substituted or unsubstituted $C_{6-20}$ aromatic hydrocarbon group, for example a tetravalent linker of the formulas

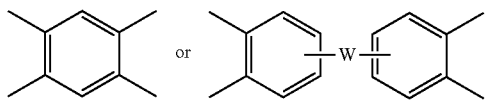

wherein W is a single bond, —O—, —S—, —C(O)—, —SO$_2$—, —SO—, a $C_{1-18}$ hydrocarbylene group, —P($R^a$)(═O)— wherein $R^a$ is a $C_{1-8}$ alkyl or $C_{6-12}$ aryl, or —$C_yH_{2y}$— wherein y is an integer from 1 to 5 or a halogenated derivative thereof (which includes perfluoroalkylene groups). These additional structural imide units preferably comprise less than 20 mol % of the total number of units, and more preferably can be present in amounts of 0 to 10 mol % of the total number of units, or 0 to 5 mol % of the total number of units, or 0 to 2 mole % of the total number of units. In some embodiments, no additional imide units are present in the polyetherimide.

In some embodiments, the polyetherimide is a polyetherimide-siloxane copolymer including the above-described polyetherimide repeating units and siloxane blocks containing units of formula (9)

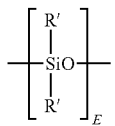

(9)

wherein E has an average value of 2 to 100, 2 to 31, 5 to 75, 5 to 60, 5 to 15, or 15 to 40, and each R' is independently a $C_{1-13}$ monovalent hydrocarbyl group. For example, each R' can independently be a $C_{1-13}$ alkyl group, $C_{1-13}$ alkoxy group, $C_{2-13}$ alkenyl group, $C_{2-13}$ alkenyloxy group, $C_{3-6}$ cycloalkyl group, $C_{3-6}$ cycloalkoxy group, $C_{6-14}$ aryl group, $C_{6-10}$ aryloxy group, $C_{7-13}$ arylalkyl group, $C_{7-13}$ arylalkoxy group, $C_{7-13}$ alkylaryl group, or $C_{7-13}$ alkylaryloxy group. The foregoing groups can be fully or partially halogenated with fluorine, chlorine, bromine, or iodine, or a combination comprising at least one of the foregoing. In an embodiment no bromine or chlorine is present, and in another embodiment no halogens are present. Combinations of the foregoing R groups can be used in the same copolymer. In an embodiment, the polysiloxane block comprises R' groups that have minimal hydrocarbon content. In a specific embodiment, an R' group with a minimal hydrocarbon content is a methyl group.

The polyetherimide-siloxane copolymers can be formed by polymerization of the oxydiphthalic anhydride (1) and a diamine component comprising an organic diamine (5) as described above or mixture of diamines, and a polysiloxane diamine of formula (10)

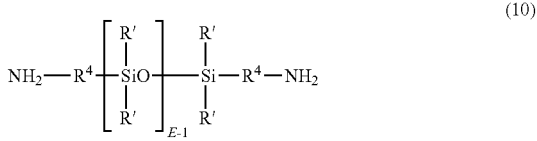

(10)

wherein R' and E are as described in formula (9), an each $R^4$ is independently a $C_2$-$C_{20}$ hydrocarbon moiety, in particular a $C_2$-$C_{20}$ arylene, alkylene, or arylenealkylene group. In an embodiment $R^4$ is a $C_2$-$C_{20}$ alkylene group, specifically a $C_2$-$C_{10}$ alkylene group such as propylene, and E has an average value of 5 to 100, 5 to 75, 5 to 60, 5 to 15, or 15 to 40. Procedures for making the polysiloxane diamines of formula (10) are well known in the art.

In some polyetherimide-siloxane copolymers the diamine component used in the manufacture of the copolymers can contain 1 to 90 mol %, or 20 to 50 mol %, or 25 to 40 mol % of polysiloxane diamine (10) and 10 to 90 mol %, or 50 to 80 mol %, or 60 to 75 mol % of diamine (5), for example as described in U.S. Pat. No. 4,404,350. The diamine components can be physically mixed prior to reaction with the bisanhydride(s), thus forming a substantially random copolymer. Alternatively, block or alternating copolymers can be formed by selective reaction of (5) and (10) with oxydiphthalic anhydrides (1), to make polyimide blocks that are subsequently reacted together. Thus, the polyetherimide-siloxane copolymer can be a block, random, or graft copolymer. Block polyetherimide-siloxane copolymers comprise etherimide blocks and siloxane blocks in the polymer backbone. The etherimide blocks and the siloxane blocks can be present in random order, as blocks (i.e., AABB), alternating (i.e., ABAB), or a combination thereof. Graft polyetherimide-siloxane copolymers are non-linear copolymers comprising the siloxane blocks connected to linear or branched polymer backbone comprising etherimide blocks.

In an embodiment, the polyetherimide-siloxane copolymer has units of formula (11)

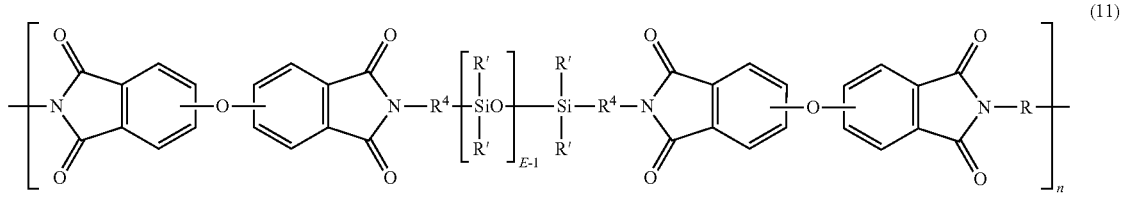

(11)

wherein R' and E of the siloxane are as in formula (9), the R 9 of the imide is as in formula (5), $R^4$ is the same as $R^4$ as in formula (10), and n is an integer from 5 to 100. In a specific embodiment, the R is a phenylene, $R^4$ is n-propylene, E is 2 to 100, 5 to 30, or 10 to 40, n is 5 to 100, and each R' of the siloxane is methyl.

The relative amount of polysiloxane units and etherimide units in the polyetherimide-siloxane copolymer depends on the desired properties, and are selected using the guidelines provided herein. In particular, the polyetherimide-siloxane copolymer is selected to have a certain average value of E, and is selected and used in amount effective to provide the desired weight percent of siloxane units. In an embodiment the polyetherimide-siloxane comprises 5 to 50 wt %, 10 to 40 wt %, or 20 to 35 wt % siloxane units, based on the total weight of the polyetherimide-siloxane. In some embodiments the polysiloxane block of the copolymer has a number average molecular weight (Mn) of 300 to 3000 grams/mole (Daltons).

The polyetherimide can exhibit one or more advantageous properties as a result of the use of the purified oxydiphthalic anhydride for its preparation. For example, the resulting polyetherimide can exhibit improved melt stability and improved relative thermal index (RTI). For example, the polyetherimide can have a RTI of less than 170° C., determined according to Underwriting Laboratories (UL protocol UL746B). The polyetherimide can exhibit a RTI of greater than 0 to less than 170° C., preferably 50 to 160° C., more preferably 100 to 160° C., as determined according to UL746B. RTI is a property that is indicative of how the polyetherimide composition's properties degrade after being subjected to heat aging. The RTI can be obtained directly by performing the extended test in accordance with the UL746B protocol, or can be indirectly inferred with an accelerated heat aging testing method. Briefly, the RTI is inferred by comparing the peak molecular weight (Mp) degradation (decrease) of an experimental sample with the peak (Mp) degradation of a control sample that is a polyetherimide made by a method in which the polyetherimide is made from bisphenol-A dianhydride, phthalic anhydride and meta-phenylene diamine that has been verified to have a RTI of greater than or equal to 170° C. by UL protocol UL746B. When the percent peak molecular weight degradation of an experimental sample is within 10% of the percent peak molecular weight degradation of the control sample, the RTI of the experimental sample is said to have the same RTI of the control sample, which is greater than or equal to 170° C. By contrast, when the percent peak molecular weight degradation of an experimental sample is greater than 10% of the percent peak molecular weight degradation of the control sample that is a polyetherimide made from a dianhydride and meta-phenylene diamine, the RTI of the experimental sample is said to have a RTI of less than 170° C., e.g., 160° C. For example, if the peak molecular weight (Mp) drop of a control sample at 230° C. in 12 or 13 days is 8%, then a resin with less than or equal to 18% Mp drop would have the equivalent RTI rating as the control sample. Indirectly determined RTI ratings are verifiable by the UL protocol UL746B. Due to the duration of the UL protocol UL746B (which can take months), it is not always practical or possible to determine the RTI rating of a candidate resin sample by UL protocol UL746B. RTI ratings indirectly obtained are preferably verified by the UL protocol UL746B whenever practical.

Polyetherimides prepared from oxydiphthalic anhydrides purified according to the method disclosed herein can be useful in a wide variety of articles for various applications. Articles made from the polyetherimide can be prepared by any number of methods including shaping, foaming, extruding, thermoforming, spinning, or molding. Examples of applications for the articles include food service, medical, lighting, lenses, sight glasses, windows, enclosures, safety shields, cookware, medical devices, trays, plates, handles, helmets, animal cages, electrical connectors, enclosures for electrical equipment, engine parts, automotive engine parts, lighting sockets and reflectors, electric motor parts, power distribution equipment, communication equipment, computers, and the like. Articles can include, for example, hollow fibers, hollow tubes, hollow tube fibers wherein the wall of the fiber has small openings of various pore sizes which affords a permeable membrane fiber, permeable membranes in other shapes with various pore sizes, solid fibers, sheets, films, multilayer sheets, multilayer films, molded parts, extruded profiles, coated parts, foams, windows, luggage racks, wall panels, chair parts, lighting panels, diffusers, shades, partitions, lenses, skylights, lighting devices, reflectors, ductwork, cable trays, conduits, pipes, cable ties, wire coatings, electrical connectors, air handling devices, ventilators, louvers, insulation, bins, storage containers, doors, hinges, handles, sinks, mirror housing, mirrors, toilet seats, hangers, coat hooks, shelving, ladders, hand rails, steps, carts, trays, cookware, food service equipment, medical devices, data transmission equipment, powders, composites, communications equipment and instrument panels, and the like.

An improved method for the purification of an oxydiphthalic anhydride is provided herein. The method advantageously employs use of a carefully selected solvent in order to solubilize any impurities, but not the desired oxydiphthalic anhydride product, thereby increasing purity without a substantial decrease in product yield. Thus, the oxydiphthalic anhydride can have substantially reduced amounts of impurities such as reaction starting materials, by products, and side products resulting from the preparation of the oxydiphthalic anhydride, and can be isolated in high yields. Therefore, a substantial improvement in methods of purifying an oxydiphthalic anhydride is provided.

This disclosure is further illustrated by the following examples, which are non-limiting.

Examples

Materials used for the following examples are described in Table 1.

TABLE 1

| Material | Description | Source |
|---|---|---|
| ODPA | 4,4'-Oxydiphthalic anhydride, CAS Reg. No. 1823-59-2 | SABIC |
| ODTA | 4,4'-Oxydiphthalic acid, CAS Reg. No. 7717-76-2 | SABIC |
| 4-ClPA | 4-Chlorophthalic anhydride, CAS Reg. No. 118-45-6 | SABIC |
| HEGCl | Hexaethylguanidinium chloride, CAS Reg. No. 69082-76-4 | Sigma-Aldrich |
| $K_2CO_3$ | Potassium carbonate, CAS Reg. No. 584-08-7 | Sigma-Aldrich |
| Acetone | Acetone, CAS Reg. No. 67-64-1 | Sigma-Aldrich |
| Toluene | Toluene, CAS Reg. No. 108-88-3 | Sigma-Aldrich |
| DMF | N,N-dimethylformamide, CAS Reg. No. 68-12-2 | Sigma-Aldrich |
| oDCB | 1,2-dichlorobenzene, CAS Reg No. 95-50-1 | Sigma-Aldrich |
| NMP | N-Methyl-2-pyrrolidone, CAS Reg. No. 872-50-04 | Sigma-Aldrich |
| EDC | 1,2 Dichloroethane, CAS Reg No. 107-06-2 | Sigma-Aldrich |
| MeOH | Methanol, CAS Reg. No. 67-56-1 | Sigma-Aldrich |

TABLE 1-continued

| Material | Description | Source |
|---|---|---|
| Ethyl Acetate | Ethyl Acetate, CAS Reg. No. 141-78-6 | Sigma-Aldrich |
| MEK | Methyl ethyl ketone, CAS Reg. No. 78-93-3 | Sigma-Aldrich |
| Diethyl ether | Diethyl ether, CAS Reg. No. 60-29-7 | Sigma-Aldrich |
| TPPBr | Tetraphenylphosphonium Bromide, CAS Reg. No. 2751-90-8 | Sigma-Aldrich |
| DCM | 1,2 dichloromethane, CAS Reg No. 75-09-2 | Sigma-Aldrich |
| Aceto-nitrile | Acetonitrile, CAS Reg No. 75-05-8 | Sigma-Aldrich |
| THF | Tetrahydrofuran, CAS Reg. No. 109-99-9 | Sigma-Aldrich |
| IPA | 2-Propanol, CAS Reg. No. 67-63-0 | Sigma-Aldrich |

Synthesis and Purification of ODPA by Hydrolysis Ring Closure (HRC)

A four necked round bottom flask equipped with a mechanical stirrer, nitrogen inlet, auger (for solid addition) and Dean-Stark apparatus with reflux condenser, was charged with 4-chlorophthalic anhydride (32 grams, 0.18 moles). Dry ortho-dichlorobenzene (ODCB) (180 milliliters) was added to the flask, which was then purged with nitrogen. The flask was heated to 210° C. by an external oil bath to remove trace moisture by Dean-Stark apparatus. The inside temperature was maintained around 180° C. After 15 minutes, the 4-ClPA was dissolved in the ODCB, forming a clear solution. The ODCB solvent collected in the overheads was analyzed for moisture by Karl Fischer titration. The moisture specification should be less than 30 ppm in the condensed oDCB condensate. Hexaethylguanidinium chloride (HEGCl) (20% w/w in ODCB) (4.7 milliliters, 0.02 equiv.) was added to the reaction mixture and dried by azeotropic distillation with ODCB. The moisture specification was maintained at 15 ppm in the overhead condensed distillate. The amount of solvent in the reaction vessel was maintained at about 80 milliliters prior to $K_2CO_3$ addition. Potassium carbonate (pre-dried in vacuum oven at 220° C. and −25 mbar for 12 hours) (12.12 grams, 0.09 moles) was added slowly to the reaction mixture over 2 hours using the auger with a nitrogen blanket to maintain an inert atmosphere. The reaction is an exothermic reaction. Temperature of the reaction mixture was maintained at 220° C. (bath temperature) while maintaining the nitrogen flow. The temperature in the reaction vessel was maintained at about 180-190° C., and stirring was continued for 3 hours. The reaction was monitored with HPLC until substantially all of the 4-ClPA content was depleted (i.e., the amount of 4-ClPA was less than or equal to 5%). The reaction mixture was cooled to 25° C. slowly and kept for 5 hours at that temperature so that ODPA and potassium chloride (KCl) precipitated from the ODCB solution. The reaction mixture was homogenized and filtered through Whatmann 1 filter paper and the resulting cake (composed primarily of KCl and ODPA) was washed with 20 milliliters (10 milliliter×2 washes) of cold ODCB.

A two-necked, round-bottomed flask was equipped with a mechanical stirrer and Dean-Stark apparatus topped with reflux condenser, and the crude ODPA/KCl material prepared in the previous reaction was added to 100 milliliters of deionized water and 8 milliliters of ortho-phosphoric acid (85%) was added to the flask. The mixture was stirred at 100° C. for 1-2 hours. The reaction was monitored by thin layer chromatography (TLC) and HPLC. After completion of the reaction, the reaction mass was cooled to 25° C. and filtered through Whatmann 1 filter paper. The solid filtrate (ODTA) was washed with cold deionized water (5×25 milliliters) to remove KCl from the ODTA) until the final filtrate gave a negative $AgNO_3$ test. The $AgNO_3$ test was conducted by taking about 5 milliliters of filtrate in a test tube with 2-3 drops of dilute nitric acid and 2-3 drops of silver nitrate solution (0.02 wt % in deionized water) was then added to the test tube. The formation of white precipitate indicated the presence of chloride ions. The lack of a white precipitate indicates that the solution does not contain chloride ions in an amount detectable by this method, and is considered to be a "negative" result for the silver nitrate test.

In a three necked round bottom flask equipped with a mechanical stirrer, nitrogen inlet and Dean-Stark apparatus topped with a reflux condenser, the crude ODTA and 150 milliliters of dry ODCB were added, and the mixture was refluxed at 220° C. to remove moisture first from the crude sample. At 220° C., ODTA was dissolved in the ODCB within 20 minutes. After removing the moisture for 45 minutes to reach the desired moisture specification (about 50 ppm in the overhead condensed distillate), the mixture was refluxed for an additional 3 hours while monitoring the reaction by HPLC to ensure the complete ring closure of ODTA to the ODPA product. The reaction mixture was cooled to 25° C. slowly to precipitate ODPA from the ODCB solution. After 5 hours at 25° C., the mixture containing precipitated ODPA was homogenized and filtered through Whatmann 1 filter paper, and washed with 20 milliliters (10 milliliters×2 washes) of cold ODCB. The ODPA filtered solid was dried in vacuum oven at 120° C. for 8 hours. Isolated yield of the product was 19.6 grams (72%).

Synthesis and Purification of ODPA by Hot Filtration (HF)

A four-necked, round-bottomed flask was equipped with a mechanical stirrer, nitrogen inlet, auger (for solid addition) and Dean-Stark apparatus topped with a reflux condenser, and was then charged with 4-chlorophthalic anhydride (32 grams, 0.18 moles). Dry ortho-dichlorobenzene (ODCB) (180 milliliters) was added to the flask, which was then purged with nitrogen. The flask was heated to 210° C. by an external oil bath to remove trace moisture by Dean-Stark apparatus. The inside temperature was maintained around 180° C. After 15 minutes, the 4-ClPA was dissolved in the ODCB, forming a clear solution. The ODCB solvent collected in the overheads was analyzed for moisture by Karl Fischer titration. The moisture specification should be less than 30 ppm in the overhead condensed oDCB distillate. Hexaethylguanidinium chloride (HEGCl) (20% w/w in ODCB, 4.7 milliliters, 0.02 molar equiv.) was added to the reaction mixture and dried by azeotropic distillation with ODCB. The moisture specification was maintained at 15 ppm in the overhead condensed distillate. The amount of solvent in the reaction vessel was maintained at about 80 milliliters prior to $K_2CO_3$ addition. Potassium carbonate (pre-dried in vacuum oven at 220° C. and −25 mbar for 12 hours, 12.12 grams, 0.09 moles) was added slowly to the reaction mixture over 2 hours using the auger with a nitrogen blanket to maintain an inert atmosphere. The reaction is an exothermic reaction. Temperature of the reaction mixture was maintained at 220° C. (bath temperature) while maintaining the nitrogen flow. The temperature in the reaction vessel was maintained at about 180-190° C., and stirring was continued for 3 hours. The reaction was monitored with HPLC until substantially all of the 4-ClPA content was depleted (i.e., until the amount of 4-ClPA was less than or equal to about 5%). The hot solution (about 180° C.) was then filtered through a sintered funnel (porosity grade G3 used, pore size is 15-40 micrometers) quickly, and washed with hot oDCB (2×10 milliliters). The KCl collected in the funnel was washed with hot oDCB to dissolve any recoverable ODPA product. The filtrate was cooled to room temperature, whereupon the desired ODPA precipitated and was collected by filtration.

The hot filtered ODPA was washed with methanol (2×10 milliliters) to remove impurities. The filtered ODPA solid was dried in a vacuum over at 120° C. for 8 hours. The isolated yield of the product was in the range of 75-85%.

A similar procedure was also followed with TPPBr as the catalyst at the same molar amount as was used with HEGCl. Samples from this reaction were washed with methanol and analyzed by HPLC to evaluate the effect of catalyst removal by solvent wash method. The isolated yield of the product was 70% using the TPPBr catalyst.

ODPA Sample Preparation

Samples of ODPA prepared by the above-described HRC or the HF process using HEGCl as the catalyst (purity by HPLC method 90%) were spiked with various impurities (CIPA, HEGCl, and ODTA), and the resulting mixtures were slurried using different solvents. The slurries were first stirred at room temperature (25° C.) for 2 hours, then filtered through a sintered funnel. The filtrate was analyzed by an HPLC method to determine the amount of impurities washed away from the product (ODPA). For each mixture, the solid content of the slurry was maintained at 10, 20, and 30 weight percent solids, where "weight percent solids" is defined as the weight of the solid OPDA used to prepare the slurry compared to the total weight of the solid ODPA and the solvent used to prepare the slurry.

Solvent Selection

The following examples were conducted to demonstrate that certain solvents can be used for the purification of ODPA prepared by both the HRC and HF processes. The suitability of a particular solvent is based on the solubility of the reactants, byproducts, reaction intermediates and catalyst. Compositions were made according to the sample preparation procedure described above. The solubility of the components in various solvents is shown in Table 2.

TABLE 2

| Solvent | 4-ClPA | ODTA | ODPA | HEGCl |
|---|---|---|---|---|
| Acetone | ++ | +− | X | − |
| MeOH | ++ | ++ | X | ++ |
| NMP | ++ | ++ | ++ | ++ |
| DMF | ++ | ++ | ++ | ++ |
| EDC | +− | X | X | ++ |
| Ether | X | X | X | X |
| DCM | +− | X | X | ++ |
| Ethyl Acetate | ++ | X | X | ++ |
| Acetonitrile | ++ | +− | +− | +− |
| oDCB | ++ | +− | +− | ++ |

In Table 2, "++" indicates that the component was soluble in the solvent at room temperature (25° C.), "+−" indicates that the component was sparingly soluble in the solvent at room temperature, "X" indicates the component was insoluble at room temperature, and "−" indicates that the particular component/solvent combination was not tested.

As can be seen from Table 2, methanol effectively dissolved each of the reactants, the catalyst, and the reaction intermediates without dissolving the ODPA product.

The following examples demonstrate the solubility of individual impurities at room temperature in the presence of ODPA prepared according to the HRC procedure. Compositions were made as described above, and are summarized in Table 3. ODPA was spiked with a known weight of 4-ClPA, ODTA, and HEGCl in different solvents (methanol or tetrahydrofuran), and stirred at room temperature for 2 to 3 hours. The compositions had a solids content of 10%, 20%, and 30% before stirring was initiated. The solution was filtered, and the filtrate was analyzed by HPLC for impurities. In the Tables below, "ODDA" refers to 4,4'-oxydiphthalic diacid The results of the HPLC analyses are also shown in Table 3.

TABLE 3

| | | Solids | Starting Composition (prior to washing) | | | | Composition of Filtrate After Washing (determined by HPLC) | | | | |
|---|---|---|---|---|---|---|---|---|---|---|---|
| Ex | Solvent | Content (%) | ODPA (wt %) | 4-ClPA (wt %) | HEGCl (wt %) | ODTA (wt %) | ODPA (wt %) | 4-ClPA (wt %) | HEGCl (wt %) | ODTA (wt %) | ODDA (wt %) |
| 1 | MeOH | 10 | 100 | 0 | 0 | 0 | 0.00 | 0.00 | 0.00 | 83.90 | 16.10 |
| 2 | MeOH | 10 | 99 | 1 | 0 | 0 | 0.00 | 8.57 | 0.00 | 75.85 | 15.58 |
| 3 | MeOH | 10 | 99 | 0 | 1 | 0 | 0.00 | 0.00 | 7.69 | 76.54 | 15.77 |
| 4 | MeOH | 10 | 99 | 0 | 0 | 1 | 0.00 | 0.00 | 0.00 | 84.77 | 15.23 |
| 5 | THF | 10 | 100 | 0 | 0 | 0 | 44.74 | 0.00 | 0.00 | 5.52 | 49.74 |
| 6 | THF | 10 | 99 | 1 | 0 | 0 | 46.21 | 4.05 | 0.00 | 4.54 | 45.20 |
| 7 | THF | 10 | 99 | 0 | 1 | 0 | 31.15 | 0.00 | 3.40 | 21.95 | 43.50 |
| 8 | THF | 10 | 99 | 0 | 0 | 1 | 40.39 | 0.00 | 0.00 | 7.09 | 52.52 |
| 9 | MeOH | 20 | 100 | 0 | 0 | 0 | 0.00 | 0.00 | 0.00 | 83.90 | 16.10 |
| 10 | MeOH | 20 | 99 | 1 | 0 | 0 | 0.00 | 9.91 | 0.00 | 76.51 | 13.57 |
| 11 | MeOH | 20 | 99 | 0 | 1 | 0 | 0.00 | 0.00 | 8.71 | 75.47 | 15.82 |
| 12 | MeOH | 20 | 99 | 0 | 0 | 1 | 0.00 | 0.00 | 0.00 | 86.42 | 13.58 |
| 13 | THF | 20 | 100 | 0 | 0 | 0 | 44.74 | 0.00 | 0.00 | 5.52 | 49.74 |
| 14 | THF | 20 | 99 | 1 | 0 | 0 | 29.96 | 4.46 | 0.00 | 13.27 | 52.31 |
| 15 | THF | 20 | 99 | 0 | 1 | 0 | 25.87 | 0.00 | 3.91 | 28.38 | 41.85 |
| 16 | THF | 20 | 99 | 0 | 0 | 1 | 25.28 | 0.00 | 0.00 | 19.56 | 55.16 |
| 17 | MeOH | 30 | 100 | 0 | 0 | 0 | 0.00 | 0.00 | 0.00 | 83.90 | 16.10 |
| 18 | MeOH | 30 | 99 | 1 | 0 | 0 | 0.00 | 10.05 | 0.00 | 75.74 | 14.21 |
| 19 | MeOH | 30 | 99 | 0 | 1 | 0 | 0.00 | 0.00 | 8.80 | 75.20 | 15.99 |
| 20 | MeOH | 30 | 99 | 0 | 0 | 1 | 0.00 | 0.00 | 0.00 | 84.81 | 15.19 |
| 21 | THF | 30 | 100 | 0 | 0 | 0 | 44.74 | 0.00 | 0.00 | 5.52 | 49.74 |
| 22 | THF | 30 | 99 | 1 | 0 | 0 | 25.43 | 4.60 | 0.00 | 23.84 | 46.13 |
| 23 | THF | 30 | 99 | 0 | 1 | 0 | 16.64 | 0.00 | 4.30 | 39.63 | 39.43 |
| 24 | THF | 30 | 99 | 0 | 0 | 1 | 20.24 | 0.00 | 0.00 | 41.56 | 38.19 |

As shown in Table 3, Examples 1-16 were used to demonstrate the removal of either CIPA, ODTA, or HEGCl from the ODPA product at a solids content of 10%, 20%, or 30% in two different solvents. The results show that THF dissolves both reactant and product, leading to considerable loss in the product yield. In contrast, methanol as the solvent selectively dissolves 4-ClPA, HEGCl, and ODTA without dissolving the ODPA product.

Solubility of Multiple Impurities in the Presence of ODPA Prepared by HRC

The following examples study the removal of multiple impurities from ODPA produced by the HRC process. Compositions were made as described above, and are summarized in Table 4. A known weight of ODPA was spiked with a known weight of 4-ClPA, ODTA, and HEGCl and then slurried in either methanol or tetrahydrofuran, and stirred at room temperature for 2-3 hours. The compositions had a solids content of 10%, 20%, or 30%. The slurries were filtered, and the filtrate was analyzed by HPLC for impurities. The results of the HPLC analysis are also shown in Table 4.

TABLE 4

| | | Solids Content (%) | Starting Composition (prior to washing) | | | | Composition of Filtrate After Washing (determined by HPLC) | | | | |
|---|---|---|---|---|---|---|---|---|---|---|---|
| Ex | Solvent | | ODPA (wt %) | 4-ClPA (wt %) | HEGCl (wt %) | ODTA (wt %) | ODPA (wt %) | 4-ClPA (wt %) | HEGCl (wt %) | ODTA (wt %) | ODDA (wt %) |
| 25 | MeOH | 10 | 99 | 0.5 | 0.5 | 0 | 0.00 | 4.63 | 3.99 | 76.03 | 15.35 |
| 26 | MeOH | 10 | 99 | 0.5 | 0 | 0.5 | 0.00 | 3.51 | 0.00 | 81.80 | 14.69 |
| 27 | MeOH | 10 | 99 | 0 | 0.5 | 0.5 | 0.00 | 0.00 | 3.59 | 81.63 | 14.79 |
| 28 | MeOH | 10 | 99 | 0.334 | 0.334 | 0.334 | 0.00 | 2.99 | 2.52 | 80.53 | 13.96 |
| 29 | THF | 10 | 99 | 0.5 | 0.5 | 0 | 38.62 | 1.78 | 1.96 | 22.52 | 35.12 |
| 30 | THF | 10 | 99 | 0.5 | 0 | 0.5 | 38.91 | 1.58 | 0.00 | 24.09 | 35.42 |
| 31 | THF | 10 | 99 | 0 | 0.5 | 0.5 | 39.13 | 0.00 | 1.78 | 24.79 | 34.30 |
| 32 | THF | 10 | 99 | 0.334 | 0.334 | 0.334 | 38.50 | 1.05 | 1.27 | 27.38 | 31.80 |
| 33 | MeOH | 20 | 99 | 0.5 | 0.5 | 0 | 0.00 | 5.14 | 4.30 | 74.71 | 15.84 |
| 34 | MeOH | 20 | 99 | 0.5 | 0 | 0.5 | 0.00 | 5.31 | 0.00 | 79.38 | 15.31 |
| 35 | MeOH | 20 | 99 | 0 | 0.5 | 0.5 | 0.00 | 0.00 | 4.33 | 80.01 | 15.66 |
| 36 | MeOH | 20 | 99 | 0.334 | 0.334 | 0.334 | 0.00 | 3.78 | 3.31 | 77.61 | 15.30 |
| 37 | THF | 20 | 99 | 0.5 | 0.5 | 0 | 23.70 | 1.88 | 2.64 | 33.48 | 38.30 |
| 38 | THF | 20 | 99 | 0.5 | 0 | 0.5 | 24.96 | 3.20 | 0.00 | 18.79 | 53.05 |
| 39 | THF | 20 | 99 | 0 | 0.5 | 0.5 | 20.46 | 0.00 | 2.75 | 37.68 | 39.11 |
| 40 | THF | 20 | 99 | 0.334 | 0.334 | 0.334 | 25.97 | 1.52 | 1.88 | 38.19 | 32.45 |
| 41 | MeOH | 30 | 99 | 0.5 | 0.5 | 0 | 0.00 | 5.03 | 4.68 | 74.69 | 15.59 |
| 42 | MeOH | 30 | 99 | 0.5 | 0 | 0.5 | 0.00 | 7.97 | 0.00 | 78.73 | 13.30 |
| 43 | MeOH | 30 | 99 | 0 | 0.5 | 0.5 | 0.00 | 0.00 | 4.55 | 81.15 | 14.30 |
| 44 | MeOH | 30 | 99 | 0.334 | 0.334 | 0.334 | 0.00 | 4.20 | 3.09 | 77.28 | 15.43 |
| 45 | THF | 30 | 99 | 0.5 | 0.5 | 0 | 15.63 | 3.80 | 3.05 | 40.31 | 37.22 |
| 46 | THF | 30 | 99 | 0.5 | 0 | 0.5 | 20.29 | 3.24 | 0.00 | 32.89 | 43.58 |
| 47 | THF | 30 | 99 | 0 | 0.5 | 0.5 | 12.33 | 0.00 | 2.91 | 46.26 | 38.49 |
| 48 | THF | 30 | 99 | 0.334 | 0.334 | 0.334 | 18.01 | 1.69 | 2.14 | 44.46 | 33.70 |

The results show that methanol selectively dissolves 4-ClPA, HEGCl, and ODTA without dissolving the ODPA product.

Effect of Residual Catalyst on the Purification of ODPA

The following examples described in Table 5 demonstrate the effectiveness of washing ODPA prepared using two different catalysts with various solvents. The ODPA was prepared according to the above described hot filtration (HF) process. The hot-filtered ODPA (shown as Example 49 in Table 11) was then washed with various solvents at room temperature. The weight ratio of ODPA solid to solvent used for washing out the impurities was 1:3, and the purity of the washed ODPA was analyzed by HPLC. The results are summarized below in Table 5.

TABLE 5

| Example | Solvent | Catalyst | No. of washes | ODPA purity (%) | Residual Catalyst (%) | Isolated Yield after washing (%) |
|---|---|---|---|---|---|---|
| 49 | — | HEGCl | 3 | 99.47 | 0.024 | — |
| 50 | Methanol | HEGCl | 3 | 99.48 | <0.003 | 91 |

TABLE 5-continued

| Example | Solvent | Catalyst | No. of washes | ODPA purity (%) | Residual Catalyst (%) | Isolated Yield after washing (%) |
|---|---|---|---|---|---|---|
| 51 | Acetone | HEGCl | 3 | 99.49 | 0.010 | 66 |
| 52 | DCM | HEGCl | 3 | 99.49 | 0.015 | 81 |
| 53 | IPA | HEGCl | 3 | 99.52 | 0.015 | 34 |
| 54 | Ethyl Acetate | HEGCl | 3 | 99.33 | 0.015 | 7 |
| 55 | DMF | HEGCl | 3 | 99.03 | 0.024 | 41 |
| 56 | THF | HEGCl | 3 | 99.53 | 0.015 | 51 |
| 57 | — | TPPBr | 3 | 97.2 | 0.094 | — |
| 58 | Methanol | TPPBr | 3 | 97.8 | 0.084 | 85 |
| 59 | Acetone | TPPBr | 3 | 97.6 | 0.100 | 20 |
| 60 | DCM | TPPBr | 3 | 97.7 | 0.083 | 28 |
| 61 | IPA | TPPBr | 3 | 97.8 | 0.084 | 48 |
| 62 | Ethyl Acetate | TPPBr | 3 | 97.7 | 0.088 | 34 |
| 63 | DMF | TPPBr | 3 | 96.4 | 0.091 | 15 |
| 64 | THF | TPPBr | 3 | 97.7 | 0.085 | 43 |

Examples 49 and 57 in Table 5 are control samples of hot-filtered ODPA that were not subjected to additional washing steps. From Table 5, it can be seen that the ODPA purity of these samples determined by HPLC was 99.47 and 97.2%, respectively, and the samples included 0.024 and 0.094% of residual catalyst. As shown in examples 49-56, washing the ODPA with methanol provided an ODPA purity of 99.48%, and a significantly decreased amount of residual catalyst (<0.003%, compared to 0.024% in the unwashed control sample). In contrast, samples washed with other solvents including acetone, DCM, isopropanol, ethyl acetate, DMF, and THF did not reduce the level of residual catalyst to the same extent. Furthermore, due to the solubility of the ODPA product in these solvents, the isolated yield after washing was significantly reduced to 81% (example 52) or less. In contrast, washing the ODPA with methanol provided an isolated yield of 91%. It is noted that the some loss in yield can be attributed to mechanical losses of product due to conducting these experiments on a small scale.

Examples 57-64 show the effect of washing ODPA prepared with TPPBr. As can be seen in Table 5, there was no significant change in the ODPA purity. Additionally, the level of residual catalyst was 0.083 to 0.1 for all samples. The isolated yields, however, were impacted, with the methanol-washed sample of example 58 giving a yield of 85%, while the other solvents tested gave yields of 15-48%. Thus the results shown in Table 5 show that methanol effectively removes HEGCl catalyst more so than a TPPBr catalyst without dissolving the ODPA product.

Effect of Methanol Washing on Purity and Color of ODPA

The following examples demonstrate the effectiveness of the methanol treatment to improve the purity and color of the ODPA compared to other purification methods.

The results are shown in Table 6. "ODPA Sigma" is 4,4'-oxydiphthalic anhydride obtained from Sigma Aldrich Chemical Company. "ODPA-HRC" is ODPA prepared as described above using the HRC method. "ODPA-oDCB-HRC" is ODPA prepared by HRC method and further washed with hot oDC. "ODPA-MeOH—HRC" is ODPA prepared by HRC method and further washed with methanol. "ODPA-oDCB-HF" is ODPA purified using hot filtration method described above. "ODPA-MeOH—HF" is ODPA prepared by the hot filtration method and further washed with methanol. "ODPA-SRI" is 4,4'-oxydiphthalic anhydride obtained from Shanghai Research Institute, China.

APHA values were determined using a 10 wt % solution of each sample in DMF, and a Macbeth colorimeter. Also shown in Table 6 is the effect of methanol washing on the purity of the ODPA product, studied by HPLC. Specifically, it can be seen in Table 6 that amounts of residual catalyst and reaction intermediate were effectively reduced by the methanol treatment without hydrolyzing the ODPA product. The methanol wash can effectively remove various intermediates including ODTA and ODDA, which can be present in ODPA. ODTA and ODDA levels in the washed ODPA were 0.3% and 2.7%, respectively. Prior to washing with methanol, the purity of the ODPA was about 87%, and it was improved to 97% after washing. The isolated yield of the methano-washed ODPA was improved to 91%.

TABLE 6

| Example | Sample | ODPA (wt %) | ODTA (wt %) | ODDA (wt %) | APHA Value |
|---|---|---|---|---|---|
| 65 | ODPA Sigma | 95.2 | 1.9 | 2.9 | 140 |
| 66 | ODPA-HRC | 89.8 | 6.6 | 3.3 | 196 |
| 67 | ODPA-oDCB-HRC | 93.7 | 4 | 1.3 | 178 |
| 68 | ODPA-MeOH-HRC | 97 | 0.3 | 2.7 | 137 |
| 69 | ODPA-MeOH-HF | ND | ND | ND | 135 |
| 70 | ODPA-oDCB-HF | ND | ND | ND | 170 |
| 71 | ODPA-SRI | ND | ND | ND | 135 |

"ND" means not determined.

The color stability of the ODPA after subjecting the ODPA to heat treatment was also examined. The heat stability testing was performed on various ODPA samples as described in Table 7. The color stability results are also shown in Table 7 below. The samples were tested using a 10 wt % solution of each sample in DMF and APHA values were recorded using a Macbeth colorimeter Each sample was heat-treated by exposing the sample to a temperature of 220 to 225° C. for about 8 hours. The samples were monitored for color changes during the heat exposure duration. Visual observations are recorded in Table 7, as well as the measured APHA color values. Example 73 ODPA exhibited a color change from white to dark brown, while no detectable color change (to the human eye) was noted for Example 72 and 74. These Examples show that the ODPA prepared by the hot filtration method using methanol as a washing solvent show good heat stability.

TABLE 7

| Example | Sample Description | Qualitative color observations after exposure to heat |
|---|---|---|
| 72 | ODPA-HRC | Dark brown in color |
| 73 | ODPA-MeOH-HF | No change observed |
| 74 | ODPA Sigma | No change observed |

This disclosure further encompasses the following non-limiting aspects.

Aspect 1: A process for purification of an oxydiphthalic anhydride, the process comprising: contacting a mixture comprising an oxydiphthalic anhydride, and at least one of a corresponding oxydiphthalic diacid, a corresponding oxydiphthalic tetraacid, a halophthalic anhydride, and a catalyst, with a solvent to provide a slurry; wherein the solvent is capable of solubilizing at least one of the corresponding oxydiphthalic diacid, the corresponding oxydiphthalic tetraacid, the halophthalic anhydride, and the catalyst at a temperature of 15 to 50° C.; and wherein the oxydiphthalic anhydride is substantially insoluble in the solvent at a temperature of 15 to 50° C.; and isolating the oxydiphthalic anhydride from the slurry.

Aspect 2: The process of aspect 1, wherein the contacting and isolating are repeated one or more times, preferably wherein the contacting and isolating are repeated until the oxydiphthalic anhydride isolated from the slurry has a purity of greater than 97%, or greater than 99%, or greater than 99.4%.

Aspect 3: The process of aspect 1 or 2, wherein the oxydiphthalic anhydride is isolated in a yield of greater than or equal to 75%, preferably greater than or equal to 80%, more preferably greater than or equal to 85%, even more preferably greater than or equal to 90%.

Aspect 4: The process of any one or more of aspects 1 to 3, wherein the oxydiphthalic anhydride comprises 4,4'-oxydiphthalic anhydride, 3,3'-oxydiphthalic anhydride, 3,4'-oxydiphthalic anhydride, or a combination comprising at least one of the foregoing, preferably 4,4'-oxydiphthalic anhydride.

Aspect 5: The process of any one or more of aspects 1 to 4, wherein the corresponding oxydiphthalic tetraacid is present and comprises 4,4'-oxydiphthalic tetraacid, 3,3'-oxydiphthalic tetraacid, 3,4'-oxydiphthalic tetraacid, or a combination comprising at least one of the foregoing, preferably 4,4'-oxydiphthalic tetraacid; or the corresponding oxydiphthalic diacid is present and comprises 4,4'-oxydiphthalic diacid, 3,3'-oxydiphthalic diacid, 3,4'-oxydiphthalic diacid, or a combination comprising at least one of the foregoing, preferably 4,4'-oxydiphthalic diacid.

Aspect 6: The process of any one or more of aspects 1 to 5, wherein the halophthalic anhydride is present and comprises 3-chlorophthalic anhydride, 4-chlorophthalic anhydride, or a combination comprising at least one of the foregoing, preferably 4-chlorophthalic anhydride.

Aspect 7: The process of any one or more of aspects 1 to 6, wherein the catalyst is present and is a phase transfer catalyst, preferably a hexaalkylguanidinium halide, a phosphonium salt, a pyridinium salt, an ammonium salt, or a combination comprising at least one of the foregoing, more preferably a hexaalkylguanidinium halide.

Aspect 8: The process of any one or more of aspects 1 to 7, wherein the catalyst is present and comprises hexaethylguanidinium chloride.

Aspect 9: The process of any one or more of aspects 1 to 9, wherein the mixture comprises less than or equal to 5 wt %, or less than or equal to 1 wt % of at least one of the corresponding oxydiphthalic diacid, the corresponding oxydiphthalic tetraacid, the halophthalic anhydride, and the catalyst, wherein weight percent is based on the total weight of the mixture.

Aspect 10: The process of any one or more of aspects 1 to 9, wherein the solvent comprises methanol.

Aspect 11: The process of any one or more of aspects 1 to 10, wherein isolating the oxydiphthalic anhydride from the slurry comprises filtering the slurry.

Aspect 12: The process of any one or more of aspects 1 to 11, wherein the isolated oxydiphthalic anhydride comprises less than or equal to 5 wt % of the corresponding oxydiphthalic tetraacid; less than or equal to 2 wt % of the corresponding oxydiphthalic diacid; less than or equal to 1 wt % of the halophthalic anhydride; and less than or equal to 0.09 wt %, or less than 0.05 wt %, or less than 0.01 wt % of the catalyst; wherein weight percent is based on the total weight of the isolated oxydiphthalic anhydride.

Aspect 13: The process of any one or more of aspects 1 to 12, wherein the isolated oxydiphthalic anhydride has an APHA color value of less than 137 and preferably, wherein the isolated oxydiphthalic anhydride is color stable.

Aspect 14: The process of any one or more of aspects 1 to 13, wherein the mixture is a product mixture obtained by a process comprising: combining a halophthalic anhydride and an organic solvent with a catalyst to provide a first solution; adding an alkali metal carbonate to the first solution under conditions effective to provide a second solution comprising a crude oxydiphthalic anhydride product; isolating the crude oxydiphthalic anhydride product from the second solution, preferably by cooling the second solution to a temperature effective to precipitate the oxydiphthalic anhydride and filtering the second solution to provide the crude oxydiphthalic anhydride product; combining the crude oxydiphthalic anhydride product with water and an organic acid under conditions effective to hydrolyze the oxydiphthalic anhydride to the corresponding oxydiphthalic tetraacid; isolating the oxydiphthalic tetraacid; and condensing the oxydiphthalic tetraacid to provide the oxydiphthalic anhydride product mixture.

Aspect 15: The process of any one or more of aspects 1 to 13, wherein the mixture is a product mixture obtained by a process comprising: combining a halophthalic anhydride and an organic solvent with a catalyst to provide a first solution; adding an alkali metal carbonate to the first solution under conditions effective to provide a second solution comprising the oxydiphthalic anhydride; and filtering the second solution at a temperature of 180 to 200° C. to provide the oxydiphthalic product mixture.

Aspect 16: The process of aspect 1, wherein the mixture comprises 4,4'-oxydiphthalic anhydride and at least one of 4,4'-oxydiphthalic tetraacid, 4,4'-oxydiphthalic diacid, 4-chlorophthalic anhydride, and hexaethylguanidinium chloride, wherein the solvent comprises methanol; wherein isolating the oxydiphthalic anhydride comprises filtering the slurry; wherein the process further comprises repeating the contacting and the isolating one to three times to provide an isolated oxydiphthalic anhydride comprising, based on the total weight of the isolated oxydiphthalic anhydride, less than or equal to 5 wt % of 4,4'-oxydiphthalic tetraacid; less than or equal to 2 wt % of 4,4'-oxydiphthalic diacid; less than or equal to 1 wt % of 4-chlorophthalic anhydride; and less than or equal to 0.09 wt %, or less than 0.05 wt %, or less than 0.01 wt % of hexaethylguanidinium chloride; wherein the oxydiphthalic anhydride has an APHA color value of less than 137; and wherein the oxydiphthalic anhydride is isolated in a yield of greater than or equal to 90%.

Aspect 17: An oxydiphthalic anhydride prepared according to the process of any one or more of aspects 1 to 16.

Aspect 18: An oxydiphthalic anhydride comprising less than or equal to 5 wt % of a corresponding oxydiphthalic tetraacid; less than or equal to 2 wt % of a corresponding oxydiphthalic diacid; less than or equal to 1 wt % of a halophthalic anhydride; and less than or equal to 0.09 wt %, or less than 0.05 wt %, or less than 0.01 wt % of a catalyst; wherein weight percent is based on the total weight of the oxydiphthalic anhydride; and wherein the oxydiphthalic anhydride has an APHA color value of less than 137.

Aspect 19: A polyetherimide prepared by polymerizing the oxydiphthalic anhydride of aspect 17 or 18 with a diamine.

The compositions, methods, and articles can alternatively comprise, consist of, or consist essentially of, any appropriate components or steps herein disclosed. The compositions, methods, and articles can additionally, or alternatively, be formulated so as to be devoid, or substantially free, of any steps, components, materials, ingredients, adjuvants, or species that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl ($-HC=CH_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene ($-CH_2-$) or, propylene ($-(CH_2)_3-$)). "Cycloalkylene" means a divalent cyclic alkylene group, $-C_nH_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a $C_{1-9}$ alkoxy, a $C_{1-9}$ haloalkoxy, a nitro ($-NO_2$), a cyano ($-CN$), a $C_{1-6}$ alkyl sulfonyl ($-S(=O)_2$-alkyl), a $C_{6-12}$ aryl sulfonyl ($-S(=O)_2$-aryl) a thiol ($-SH$), a thiocyalkylano ($-SCN$), a tosyl ($CH_3C_6H_4SO_2-$), a $C_{3-12}$ cycloalkyl, a $C_{2-12}$ alkenyl, a $C_{5-12}$ cycloalkenyl, a $C_{6-12}$ aryl, a $C_{7-13}$ arylalkylene, a $C_{4-12}$ heterocycloalkyl, and a $C_{3-12}$ heteroaryl instead of hydrogen, provided that the substituted atom's normal valence is not exceeded. The number of carbon atoms indicated in a group is exclusive of any substituents. For example $-CH_2CH_2CN$ is a $C_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A process for purification of an oxydiphthalic anhydride, the process comprising:
    contacting a mixture comprising
        an oxydiphthalic anhydride, and
        at least one of a corresponding oxydiphthalic diacid, a corresponding oxydiphthalic tetraacid, a halophthalic anhydride, and a catalyst,
    with a solvent comprising methanol to provide a slurry;
    wherein the solvent is capable of solubilizing at least one of the corresponding oxydiphthalic diacid, the corresponding oxydiphthalic tetraacid, the halophthalic anhydride, and the catalyst at a temperature of 15 to 50° C.; and
    wherein the oxydiphthalic anhydride is substantially insoluble in the solvent at a temperature of 15 to 50° C.; and
    isolating the oxydiphthalic anhydride from the slurry.

2. The process of claim 1, wherein the contacting and isolating are repeated one or more times, preferably wherein the contacting and isolating are repeated until the oxydiphthalic anhydride isolated from the slurry has a purity of greater than 97%.

3. The process of claim 1, wherein the oxydiphthalic anhydride is isolated in a yield of greater than or equal to 75%.

4. The process of claim 1, wherein the oxydiphthalic anhydride comprises 4,4'-oxydiphthalic anhydride, 3,3'-oxydiphthalic anhydride, 3,4'-oxydiphthalic anhydride, or a combination comprising at least one of the foregoing.

5. The process of claim 1, wherein
the corresponding oxydiphthalic tetraacid is present and comprises 4,4'-oxydiphthalic tetraacid, 3,3'-oxydiphthalic tetraacid, 3,4'-oxydiphthalic tetraacid, or a combination comprising at least one of the foregoing; or
the corresponding oxydiphthalic diacid is present and comprises 4,4'-oxydiphthalic diacid, 3,3'-oxydiphthalic diacid, 3,4'-oxydiphthalic diacid, or a combination comprising at least one of the foregoing; or
the halophthalic anhydride is present and comprises 3-chlorophthalic anhydride, 4-chlorophthalic anhydride, or a combination comprising at least one of the foregoing; or
the catalyst is present and is a phase transfer catalyst.

6. The process of claim 1, wherein the catalyst is present and comprises hexaethylguanidinium chloride.

7. The process of claim 1, wherein the mixture comprises less than or equal to 5 wt % of at least one of the corresponding oxydiphthalic diacid, the corresponding oxydiphthalic tetraacid, the halophthalic anhydride, and the catalyst, wherein weight percent is based on the total weight of the mixture.

8. The process of claim 1, wherein isolating the oxydiphthalic anhydride from the slurry comprises filtering the slurry.

9. The process of claim 1, wherein the isolated oxydiphthalic anhydride comprises, based on the total weight of the isolated oxydiphthalic anhydride,
less than or equal to 5 wt % of the corresponding oxydiphthalic tetraacid;
less than or equal to 2 wt % of the corresponding oxydiphthalic diacid;
less than or equal to 1 wt % of the halophthalic anhydride; and
less than or equal to 0.09 wt % of the catalyst; and
wherein the isolated oxydiphthalic anhydride has an APHA color value of less than 137.

10. The process of claim 1, wherein the mixture is a product mixture obtained by a process comprising:
combining a halophthalic anhydride and an organic solvent with a catalyst to provide a first solution;
adding an alkali metal carbonate to the first solution under conditions effective to provide a second solution comprising a crude oxydiphthalic anhydride product;
isolating the crude oxydiphthalic anhydride product from the second solution;
combining the crude oxydiphthalic anhydride product with water and an organic acid under conditions effective to hydrolyze the oxydiphthalic anhydride to the corresponding oxydiphthalic tetraacid;
isolating the oxydiphthalic tetraacid; and
condensing the oxydiphthalic tetraacid to provide the oxydiphthalic anhydride product mixture.

11. The process of claim 1, wherein the mixture is a product mixture obtained by a process comprising:
combining a halophthalic anhydride and an organic solvent with a catalyst to provide a first solution;
adding an alkali metal carbonate to the first solution under conditions effective to provide a second solution comprising the oxydiphthalic anhydride; and
filtering the second solution at a temperature of 180 to 200° C. to provide the oxydiphthalic product mixture.

12. The process of claim 1,
wherein the mixture comprises 4,4'-oxydiphthalic anhydride and at least one of 4,4'-oxydiphthalic tetraacid, 4,4'-oxydiphthalic diacid, 4-chlorophthalic anhydride, and hexaethylguanidinium chloride,
wherein the solvent comprises methanol;
wherein isolating the oxydiphthalic anhydride comprises filtering the slurry;
wherein the process further comprises repeating the contacting and the isolating one to three times to provide an isolated oxydiphthalic anhydride comprising, based on the total weight of the isolated oxydiphthalic anhydride,
less than or equal to 5 wt % of 4,4'-oxydiphthalic tetraacid;
less than or equal to 2 wt % of 4,4'-oxydiphthalic diacid;
less than or equal to 1 wt % of 4-chlorophthalic anhydride; and
less than or equal to 0.09 wt % of hexaethylguanidinium chloride;
wherein the oxydiphthalic anhydride has an APHA color value of less than 137;
wherein the oxydiphthalic anhydride is color stable; and
wherein the oxydiphthalic anhydride is isolated in a yield of greater than or equal to 90%.

* * * * *